United States Patent [19]

Rusay

[11] 4,202,685
[45] May 13, 1980

[54] 2-1-(2-HYDROXY ALKYL IMINO)-ETHYL-1-HYDROXY-4,4,6,6-TETRAMETHYL CYCLOHEXEN-3,5-DIONES

[75] Inventor: Ronald J. Rusay, Lafayette, Calif.

[73] Assignee: Stauffer Chemical Company, Westport, Conn.

[21] Appl. No.: 947,218

[22] Filed: Sep. 29, 1978

[51] Int. Cl.² .................. A01N 9/20; C07C 119/00
[52] U.S. Cl. ........................... 71/121; 260/566 R; 260/438.1; 260/439 R
[58] Field of Search ........... 71/121; 260/566 R, 438.1, 260/439 R

[56] References Cited
U.S. PATENT DOCUMENTS 3,968,161  7/1976  Schulte-Elte .................. 260/566 R

FOREIGN PATENT DOCUMENTS 5186466  7/1976  Japan.

Primary Examiner—Catherine L. Mills
Attorney, Agent, or Firm—Edwin H. Baker

[57] ABSTRACT

Compounds having the following structural formula

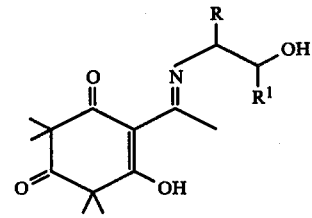

wherein R is hydrogen or alkyl and R¹ is hydrogen or alkyl which are useful as post-emergent herbicides.

8 Claims, No Drawings

2-1-(2-HYDROXY ALKYL IMINO)-ETHYL-1-HYDROXY-4,4,6,6-TETRAMETHYL CYCLOHEXEN-3,5-DIONES

BACKGROUND OF THE INVENTION

This invention relates to certain novel 2-1-(2-hydroxy alkyl imino)-ethyl-1-hydroxy-4,4,6,6-tetramethyl cyclohexen-3,5-diones as post-emergent herbicides.

DESCRIPTION OF THE INVENTION

The compounds of this invention have the following structural formula

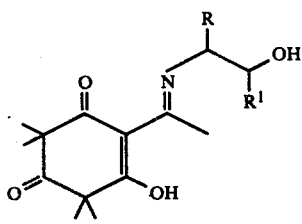

wherein R is hydrogen or alkyl having 1 to 4 carbon atoms, preferably hydrogen and $R^1$ is hydrogen or alkyl having 1 to 4 carbon atoms, preferably hydrogen.

The compounds of this invention can have the following four structural formulas because of tautomerism, R and R' being as defined.

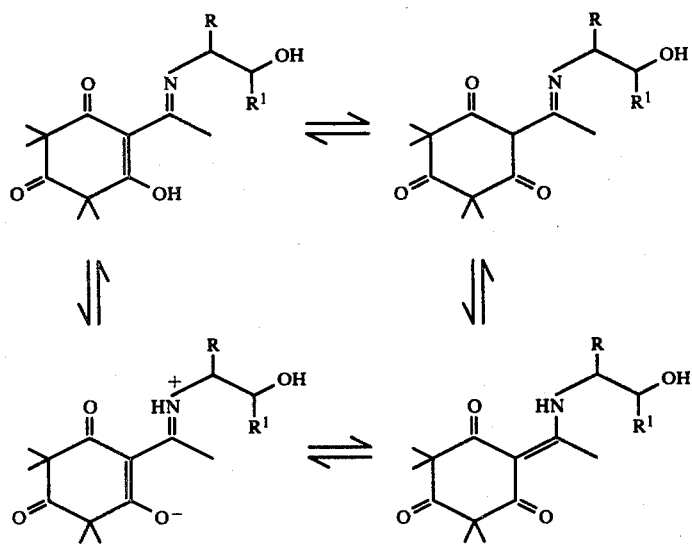

In the above description of the compounds of this invention, alkyl includes both straight chain and branched chain configurations, for example, methyl, ethyl, n-propyl, isopropyl, n-butyl, sec-butyl or tert. butyl.

The compounds of this invention are active as post-emergent herbicides on the plant genus Avena. That is, they are herbicidally effective post-emergent against this genus and especially active against the species *Avena sativa* and *Avena fatua*. The method of controlling said vegetation comprises applying a herbicidally effective amount of the above-described compounds to the area where post-emergence control of the plant genus Avena is desired.

The compounds of the present invention can be prepared by the following general method

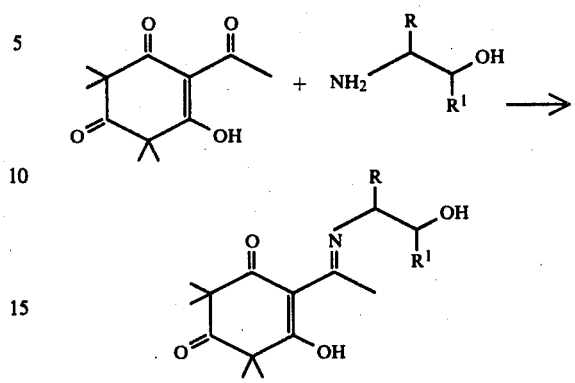

wherein R and R' are as defined.

Generally, equal molar amounts of 1-hydroxy-2-acetyl-4,4,6,6-tetramethyl cyclohexen-3,5-diones and the amino alcohol dissolved in a solvent such as toluene are refluxed with the azeotropic removal of water until no water is collected in a receiver. The solution is cooled and filtered through dicalite. The solvent is removed by evaporation to yield the desired product in high yields.

Similarly effective as herbicides are mono- and divalent salts of the above-described compounds of this invention. The monovalent metal salts have the structural formula

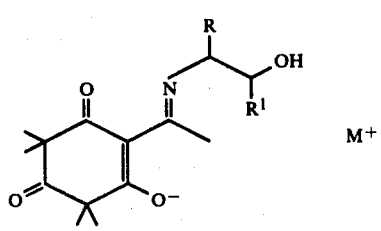

and the divalent metal salts having the structural formula

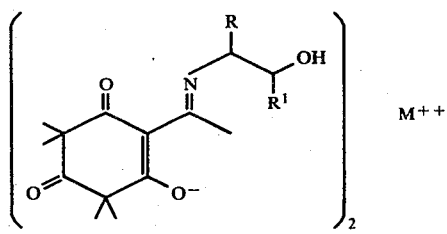

The monovalent metal ion can be any Group I metal, preferably potassium or sodium. The divalent metal ion (M++) can be any Group II-A metal, iron or copper, preferably magnesium, calcium, iron or copper.

The monovalent metal salts are easily prepared by reacting a mole of a compound of this invention as described above with about a mole of a monovalent metal hydroxide such as potassium hydroxide or sodium hydroxide.

The divalent metal salts are correspondingly prepared by reacting two moles of a compound of this invention with about a mole of divalent metal hydroxide such as calcium hydroxide or magnesium hydroxide.

For the preparation of both mono- and divalent metal salts of the compounds of this invention, the above reaction can be carried out in an organic solvent for the compound and the metal hydroxide, followed by evaporation of the solvent and water at reduced pressures. Preferred solvents are methanol, ethanol and acetone, most preferably methanol.

Preparation of the dione intermediate can be prepared according to the teaching of the following example.

EXAMPLE I

1-HYDROXY-2-ACETYL-4,4,6,6-TETRAMETHYL CYCLOHEXEN-3,5-DIONES

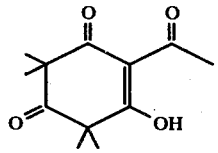

This example teaches a method of preparation for the above named reactant. First 190.3 grams (1.34 moles) of iodomethane is added dropwise to a solution of 45 grams (0.27 mole) of 2,4,6-trihydroxy acetophenone, 180 milliliters of methanol and 425 grams (1.98 moles) of a 25% sodium methoxide methanol solution which is maintained at 5°–10° C. The reaction mixture is heated for 3.5 hours and then concentrated at atmospheric pressure by distillation of iodomethane and methanol. Two hundred milliliters of water is added and the mixture is acidified with 5 N hydrochloric acid and extracted with ether. The ethereal solution is washed with 5% sodium sulfite and then water, followed by drying over sodium sulfate and evaporation of the ether. In this manner, 50 grams (83%) of 1-hydroxy-2-acetyl-4,4,6,6-tetramethyl cyclohexen-3,5-diones is prepared which has been confirmed by instrumental analysis.

EXAMPLE II 2-1-(2-HYDROXY ETHYLIMINO)-ETHYL-1-HYDROXY-4,4,6,6-TETRAMETHYL CYCLOHEXEN-3,5-DIONES

A solution of 1.03 grams (4.6 millimole) of 1-hydroxy-2-acetyl-4,4,6,6-tetramethyl cyclohexen-3,5-diones, 0.31 gram (4.6 millimole) of ethanol amine in 30 milliliters toluene was heated in a 100 milliliter flask equipped with a magnetic stirring bar and a Dean Stark trap at reflux temperature. After the azeotropic removal of water ceased, the solution was cooled. Next, the solution was filtered through dicalite (diatomaceous earth). The toluene solvent was then removed by evaporation to yield 1.26 grams (100 percent yield) of the desired compound $n_D^{30}$ 1.5245. The structure was confirmed by instrumental analysis.

The following is a table of certain selected compounds that were prepared according to the procedures described herein. Compound numbers are assigned to each compound and are used throughout the remainder of the specification.

TABLE I

| Compound Number | R | $R^1$ | $n_D^{30}$ & m.p. |
|---|---|---|---|
| 1* | H | H | 1.5245 |
| 2 | —$C_2H_5$ | H | 1.5420 |
| 3 | H | $C_4H_9$ | 1.5345 |
| 4 | H | —$C_2H_5$ | 1.5440 |
| 5 | H | —$CH_3$ | 69°–76° C. |

*Prepared in Example II

HERBICIDAL SCREENING TESTS

As previously mentioned, the herein described compounds produced in the above-described manner are phytotoxic compounds which are useful and valuable in the post-emergence control of Avena. Selected compounds of this invention are tested as such herbicides in the following manner.

POST-EMERGENCE HERBICIDE SCREEN

Seeds of the plant species red oats, *Avena sativa* along with pinto beans (*Phaseolus vulgaris* were planted in the flats across the width to give 20–50 seedlings per row. The flats were placed in the greenhouse at 70° to 85° F. and watered daily with a sprinkler. About 7 to 10 days after planting, when the primary leaves of the bean plants were almost fully expanded and the first trifoliate leaves were just starting to form, the plants were sprayed. The spray was prepared by weighing out 20 milligrams of the test compound, dissolving it in 2.5 milliliters of acetone containing 1% polyoxyethylene sorbitan monolaurate and then adding 2.5 milliliters of water. The solution was sprayed on the foliage using a No. 152 DeVilbiss atomizer at an air pressure of 5 lb./sq. inch. The spray concentration was 0.2% and the rate is 8 lb./acre. The spray volume was 238 gallon-/acre.

The injury rating from 0 to 100% was recorded for the species Avena sativa as percent control with 0% representing no injury and 100% representing complete control.

The results of this test is shown in the following Table II.

TABLE II

| Compound Number | Post-emergence Control |
| --- | --- |
| 1 | 95 |
| 2 | 40 |
| 3 | 40 |
| 4 | 20 |
| 5 | 30 |

POST-EMERGENCE WILDOAT EVALUATION

Galvanized iron flats which were 12 inches long, 8 inches wide and 3 inches deep were filled with 11 pounds of sandy loam soil which contained 75 ppm Captan ® and 50 ppm 18-18-18 fertilizer. The moisture content was about 9%. The soil was tamped and leveled and a row marker is used to impress seven rows across the width of the flat. Full rows of wild oats (Avena fatua) were planted thick enough so that several seedlings would emerge per inch of row.

The flats were placed in the greenhouse at 70°–85° F. and watered by sprinkling. Nine to 11 days after planting, the flats were sprayed on a table which is calibrated to apply 80 gallons of solution per acre. The candidate compound was applied at the rate of 2 lb ai/A. An air pressure of 33 lb/sq. inch was used to apply the spray through an 8004 E TeeJet nozzle from a reservoir which holds the solution.

The spray solution was made up by weighing out 300 milligrams of the candidate compound into a 120 milliliter wide-mouth bottle, dissolving it in 50 milliliters of acetone containing 1% Tween 20 ® polyoxyethylene sorbitan monolaurate emulsifier, and then diluting to 100 milliliters with water.

The flats were returned to the greenhouse after spraying and watered daily without wetting the foliage for three days. Thereafter, the flats were watered daily by sprinkling. Three weeks after treatment, the degree of weed control was estimated and recorded as percentage control compared to the growth of the same species in an untreated check flat of the same age.

The injury rating from 0 to 100% was recorded for the species Avena fatua as percent control with 0% representing no injury and 100% representing complete control.

The results of this test are shown in the following Table III.

TABLE III

| Compound Number | Post-emergence Control |
| --- | --- |
| 1 | 100 |
| 2 | 100 |
| 3 | * |
| 4 | 100 |
| 5 | 100 |

*Not evaluated

The compounds of the present invention are useful as post-emergence herbicides and can be applied in a variety of ways at various concentrations. In practice, the compounds herein defined are formulated into herbicidal compositions, by admixture, in herbicidally effective amounts, with the adjuvants and carriers normally employed for facilitating the dispersion of active ingredients for agricultural applications, recognizing the fact that the formulation and mode of application of a toxicant may affect the activity of the materials in a given application. Thus, these active herbicidal compounds may be formulated as granules of relatively large particle size, as wettable powders, as emulsifiable concentrates, as powdery dusts, as solutions or as any of several other known types of formulations, depending upon the desired mode of application. Preferred formulations for post-emergence herbicidal application is wettable powders, emulsifiable concentrates and granules. These formulations may contain as little as about 0.5% to as much as about 95% or more by weight of active ingredient. A herbicidally effective amount depends upon the nature of the seeds or plants to be controlled and the rate of application varies from about 0.05 to approximately 25 pounds per acre, preferably from about 0.1 to 10 pounds per acre and more preferably from about 0.1 to 3.0 pounds per acre.

Wettable powders are in the form of finely divided particles which disperse readily in water or other dispersant. The wettable powder is ultimately applied to the soil either as a dry dust or as a dispersion in water or other liquid. Typical carriers for wettable powders include fuller's earth, kaolin clays, silicas and other readily wet organic or inorganic diluents. Wettable powders normally are prepared to contain about 5% to about 95% of the active ingredient by weight and usually also contain a small amount of wetting, dispersing or emulsifying agent to facilitate wetting and dispersion.

Emulsifiable concentrates are homogeneous liquid compositions which are dispersible in water or other dispersant, and may consist entirely of the active compound with a liquid or solid emulsifying agent, or may also contain a liquid carrier, such as xylene, heavy aromatic naphthal, isophorone and other non-volatile organic solvents. For herbicidal application, these concentrates are dispersed in water or other liquid carrier and normally applied as a spray to the area to be treated. The percentage by weight of the essential active ingredient may vary according to the manner in which the composition is to be applied, but in general comprises about 0.5% to 95% of active ingredient by weight of the herbicidal composition.

Granular formulations, wherein the toxicant is carried on relatively coarse particles, are usually applied without dilution to the area in which suppression of vegetation is desired. Typical carriers for granular formulations include sand, fuller's earth, bentonite clays, vermiculite, perlite and other organic or inorganic materials which absorb or which may be coated with the toxicant. Granular formulations normally are prepared to contain about 5% to about 25% of active ingredient and may also contain small amounts of other ingredients which may include surface-active agents such as wetting agents, dispersing agents or emulsifiers; oils such as heavy aromatic naphthas, kerosene or other petroleum fractions, or vegetable oils; and/or stickers such as dextrins, glue or synthetic resins.

Typical wetting, dispersing or emulsifying agents used in agricultural formulations include, for example, the alkyl and alkylaryl sulfonates and sulfates and their sodium salts; polyhydric alcohols; and other types of surface-active agents, many of which are available in commerce. The surface-active agent, when used, normally comprises from 0.1% to 15% by weight of the herbicidal composition.

Dusts, which are free-flowing admixtures of the active ingredient with finely divided solids such as talc, clays, flours, and other organic and inorganic solids which act as dispersants and carriers for the toxicant, are useful formulations for soil-incorporating applications.

Pastes, which are homogeneous suspensions of a finely divided solid toxicant in a liquid carrier such as water or oil, are employed for specific purposes. These formulations normally contain about 5% to about 95% of active ingredient by weight, and may also contain small amounts of a wetting, dispersing or emulsifying agent to facilitate dispersion. For application, the pastes are normally diluted and applied as a spray to the area to be affected.

Other useful formulations for herbicidal applications include simple solutions of the active ingredient in a dispersant in which it is completely soluble at the desired concentration, such as acetone, alkylated naphthalenes, xylene or other organic solvents. Pressurized sprays, typically aerosols, wherein the active ingredient is dispersed in finely-divided form as a result of vaporization of a low boiling dispersant solvent carrier, such as the Freons, may also be used.

The phytotoxic compositions of this invention are applied to the plants in the conventional manner. Thus, the dust and liquid compositions can be applied to the plant by the use of power-dusters, boom and hand sprayers and spray dusters. The compositions can also be applied from airplanes as a dust or a spray because they are effective in very low dosages. In order to modify or control growth of germinating seeds or emerging seedlings, as a typical example, the dust and liquid compositions are applied to the soil according to convention methods and are distributed in the soil to a depth of at least ½ inch below the soil surface. It is not necessary that the phytotoxic compositions be admixed with the soil particles since these compositions can also be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The phytotoxic compositions of this invention can also contain other additaments, for example, fertilizers, pesticides and the like, used as adjuvant or in combination with any of the above-described adjuvants. Other phytotoxic compounds useful in combination with the above-described compounds include, for example, 2,4-dichlorophenoxyacetic acids, 2,4,5-trichlorophenoxyacetic acid, 2-methyl-4-chlorophenoxyacetic acid and the salts, esters and amides thereof; triazine derivatives, such as 2,4-bis(3-methoxypropylamino)-6-methylthio-s-triazine, 2-chloro-4-ethylamino-6-isopropylamino-s-triazine, and 2-ethylamino-4-isopropylamino-6-methylmercapto-s-triazine; urea derivatives, such as 3-(3,4-dichlorophenyl)-1,1-dimethyl urea and 3-(p-chlorophenyl)-1,1-dimethyl urea; and acetamides such as N,N-diallyl-α-chloroacetamide, and the like; benzoic acids such as 3-amino-2,5-dichlorobenzoic; thiocarbamates, such as S-propyl dipropylthiocarbamate, S-ethyl dipropylthiocarbamate, S-ethyl cyclohexylethyl thiocarbamate, S-ethyl hexahydro-1H-azepine-1-carbothioate and the like; 4-(methylsulfonyl)-2,6-dinitro-N,N-substituted anilines, such as 4-(methylsulfonyl)-2,6-dinitro-N,N-substituted anilines, such as 4-trifluoromethyl-2,6-dinitro-N,N-di-n-propyl aniline and 4-trifluoromethyl-2,6-dinitro-N-ethyl-N-n-butyl aniline. Fertilizers useful in combination with the active ingredients include, for example, ammonium nitrate, urea and superphosphate. Other useful additaments include materials in which plant organisms take root and grow such as compost, manure, humus, sand and the like.

What is claimed is:

1. A compound having the following structural formula

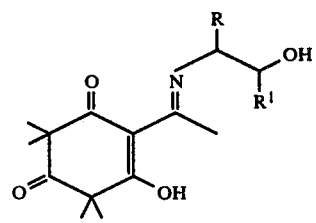

wherein R is hydrogen or alkyl having 1 to 4 carbon atoms, and $R^1$ is hydrogen or alkyl having 1 to 4 carbon atoms.

2. The compound of claim 1 wherein R is hydrogen and $R^1$ is hydrogen.

3. A method of controlling the weed genus Avena comprising applying thereto an herbicidally effective amount of a compound having the formula

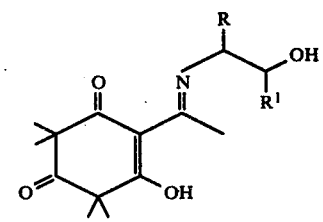

wherein R is hydrogen or alkyl having 1 to 4 carbon atoms, and $R^1$ is hydrogen or alkyl having 1 to 4 carbon atoms.

4. The method of claim 3 where R is hydrogen and $R^1$ is hydrogen.

5. A salt having the structural formula

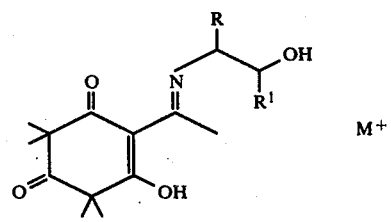

wherein R is hydrogen or alkyl having 1 to 4 carbon atoms and $R^1$ is hydrogen or alkyl having 1 to 4 carbon atoms and $M^+$ is a monovalent metal iron of Group I.

6. A salt having the structural formula

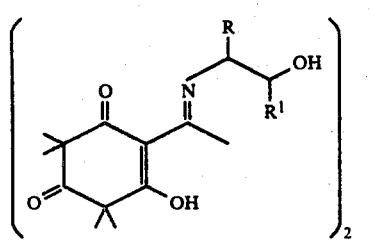

wherein R is hydrogen or alkyl having 1 to 4 carbon atoms and R¹ is hydrogen or alkyl having 1 to 4 carbon atoms and M⁺⁺ is a divalent metal ion of Group II-A, iron or copper.

7. A composition of matter consisting essentially of an effective amount of

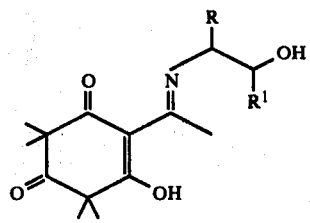

wherein R is hydrogen or alkyl having 1 to 4 carbon atoms, and R¹ is hydrogen or alkyl having 1 to 4 carbon atoms and an inert carrier therefor, said composition being active as a post-emergent herbicide on the plant genus Avena.

8. The composition of claim 7 wherein R is hydrogen and R¹ is hydrogen.

* * * * *